United States Patent
Guntzer et al.

(10) Patent No.: US 9,480,448 B2
(45) Date of Patent: Nov. 1, 2016

(54) SYSTEM AND METHOD FOR USE IN MAPPING A RADIATION DOSE APPLIED IN AN ANGIOGRAPHY IMAGING PROCEDURE OF A PATIENT

(71) Applicant: GENERAL ELECTRIC COMPANY, Schenectady, NY (US)

(72) Inventors: Pierre Guntzer, Strasbourg (FR); Vincent Pangon, Strasbourg (FR); Evrard Mukuna, Buc (FR); Jean-Baptiste Meyer, Strasbourg (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/338,464

(22) Filed: Jul. 23, 2014

(65) Prior Publication Data
US 2016/0022241 A1    Jan. 28, 2016

(51) Int. Cl.
*A61B 6/00* (2006.01)
*A61B 6/02* (2006.01)
(Continued)

(52) U.S. Cl.
CPC .............. *A61B 6/504* (2013.01); *A61B 6/022* (2013.01); *A61B 6/032* (2013.01); *A61B 6/0407* (2013.01);
(Continued)

(58) Field of Classification Search
CPC .. A61B 6/032; A61B 6/4429; A61B 6/4435; A61B 6/4441; A61B 6/481; A61B 6/482; A61B 6/503; A61B 6/504; A61B 6/542; A61B 6/545
USPC .............. 378/62, 65, 196, 197, 207, 97, 108
See application file for complete search history.

(56) References Cited

U.S. PATENT DOCUMENTS 5,027,818 A    7/1991   Bova et al.
5,354,997 A *  10/1994  Miller ..................... G01T 1/105
                                                 250/337
(Continued)

FOREIGN PATENT DOCUMENTS

EP      0 689 680      8/1998
EP      0 792 466      4/2003
(Continued)

OTHER PUBLICATIONS

International Search Report and Written Opinion for International Application No. PCT/US2015/041136, mail date Oct. 30, 2015, 10 pages.
(Continued)

*Primary Examiner* — Allen C. Ho (57) ABSTRACT

A system and method for use in mapping a radiation dose applied in an angiography imaging procedure is provided. The system can include an image acquisition system, a table in support of the patient, and a computer processor that calculates an angulation of a radiation beam to the patient in the angiography imaging procedure relative to the table; calculating an angulation of the table; calculating an intersection of the radiation beam relative to a two-dimensional grid; calculating the radiation dose applied at the intersection of the radiation beam to each of the predefined areas of the two-dimensional grid; calculating an orientation of the patient relative to the two-dimensional grid of predefined areas; and creating a graphic display illustrative of an aggregation of the radiation dose applied to each of the predefined areas of the two-dimensional grid for viewing by a user.

19 Claims, 6 Drawing Sheets

(51) Int. Cl.
*A61B 6/03* (2006.01)
*A61B 6/04* (2006.01)
*G06T 7/00* (2006.01)

(52) U.S. Cl.
CPC ........... *A61B 6/4429* (2013.01); *A61B 6/4435* (2013.01); *A61B 6/4441* (2013.01); *A61B 6/481* (2013.01); *A61B 6/482* (2013.01); *A61B 6/503* (2013.01); *A61B 6/542* (2013.01); *A61B 6/545* (2013.01); *G06T 7/00* (2013.01); *G06T 2207/10116* (2013.01)

(56) References Cited

U.S. PATENT DOCUMENTS

| | | | | |
|---|---|---|---|---|
| 5,567,948 | A * | 10/1996 | Miller | G01T 1/11 250/484.5 |
| 5,569,927 | A * | 10/1996 | Miller | G01T 1/11 250/484.5 |
| 5,635,709 | A * | 6/1997 | Sliski | G01T 1/169 250/252.1 |
| 5,761,270 | A | 6/1998 | Unfors | |
| 5,870,697 | A * | 2/1999 | Chandler | A61N 5/1031 378/62 |
| 5,954,650 | A | 9/1999 | Saito et al. | |
| D428,397 | S | 7/2000 | Palalau et al. | |
| 6,304,625 | B1 | 10/2001 | Senzig | |
| 6,435,714 | B1 * | 8/2002 | Bruder | A61B 6/032 378/196 |
| 6,469,717 | B1 | 10/2002 | Wineke et al. | |
| 6,574,500 | B2 * | 6/2003 | Keren | A61B 6/504 378/51 |
| 6,614,452 | B1 | 9/2003 | Cable | |
| D483,381 | S | 12/2003 | Platz | |
| 6,892,948 | B2 | 5/2005 | Steklenski et al. | |
| 6,918,697 | B2 | 7/2005 | Weidmann | |
| 7,054,801 | B2 * | 5/2006 | Sakamoto | A61N 5/103 250/492.3 |
| 7,098,470 | B2 * | 8/2006 | Akselrod | C30B 15/00 250/581 |
| 7,211,808 | B2 * | 5/2007 | Griggs | G01T 1/04 250/472.1 |
| 7,227,152 | B2 | 6/2007 | Brabec et al. | |
| 7,254,623 | B1 | 8/2007 | Toth | |
| 7,313,223 | B2 | 12/2007 | Unfors | |
| 7,361,908 | B2 * | 4/2008 | Fung | A61N 5/1048 250/474.1 |
| 7,399,977 | B2 | 7/2008 | Rink et al. | |
| D578,132 | S | 10/2008 | Lee | |
| 7,432,510 | B2 | 10/2008 | Yeo | |
| 7,441,955 | B2 | 10/2008 | Guyonnet et al. | |
| 7,450,687 | B2 | 11/2008 | Yeo et al. | |
| D589,527 | S | 3/2009 | Shamma | |
| 7,518,126 | B2 * | 4/2009 | Neuhaus-Steinmetz | G01J 1/50 250/474.1 |
| 7,581,191 | B2 | 8/2009 | Rice et al. | |
| 7,607,092 | B2 | 10/2009 | Rogers et al. | |
| 7,627,079 | B2 | 12/2009 | Boone | |
| 7,652,268 | B2 | 1/2010 | Patel | |
| 7,662,083 | B2 | 2/2010 | Gueye et al. | |
| D614,634 | S | 4/2010 | Nilsen | |
| D616,893 | S | 6/2010 | Ehrler et al. | |
| D622,731 | S | 8/2010 | Krum et al. | |
| 7,801,273 | B2 * | 9/2010 | Hoornaert | A61N 5/1048 378/97 |
| 7,871,406 | B2 * | 1/2011 | Nields | A61B 18/18 606/27 |
| 7,890,498 | B1 | 2/2011 | Hafey et al. | |
| 7,923,694 | B2 | 4/2011 | Black et al. | |
| 7,956,334 | B2 * | 6/2011 | Morita | C02F 1/32 250/474.1 |
| 8,063,915 | B2 * | 11/2011 | Champion | A61B 5/445 345/619 |
| 8,107,589 | B2 | 1/2012 | Sakurai et al. | |
| 8,119,978 | B2 | 2/2012 | Islam et al. | |
| 8,133,167 | B2 | 3/2012 | Gueye et al. | |
| D658,667 | S | 5/2012 | Cho et al. | |
| 8,175,894 | B2 | 5/2012 | Oowaki et al. | |
| 8,198,595 | B2 * | 6/2012 | Polishchuk | G01T 1/026 250/370.07 |
| D663,737 | S | 7/2012 | Sullivan | |
| 8,311,848 | B2 | 11/2012 | Subash et al. | |
| 8,315,355 | B2 * | 11/2012 | Mohamed | G06T 11/005 378/62 |
| D671,954 | S | 12/2012 | Wojcik et al. | |
| 8,411,925 | B2 * | 4/2013 | Fuchigami | A61B 5/02007 378/16 |
| 8,489,431 | B2 * | 7/2013 | Bourdeaux | A61B 6/00 705/2 |
| D687,457 | S | 8/2013 | Edwards et al. | |
| 8,503,613 | B2 * | 8/2013 | Sabol | A61B 6/032 378/165 |
| 8,560,968 | B1 | 10/2013 | Nair | |
| 8,563,947 | B2 * | 10/2013 | Kearfott | G01T 1/10 250/473.1 |
| D692,916 | S | 11/2013 | Granchi et al. | |
| D696,680 | S | 12/2013 | Bae et al. | |
| 8,681,935 | B2 * | 3/2014 | Ruijters | A61B 6/547 378/205 |
| 8,694,157 | B2 * | 4/2014 | Wenderow | A61B 5/7475 600/523 |
| 8,737,713 | B2 | 5/2014 | Baumgart | |
| 8,755,583 | B2 * | 6/2014 | Deuerling-Zheng | A61B 6/481 378/62 |
| 8,774,361 | B2 * | 7/2014 | Kargar | A61B 6/107 378/204 |
| 8,790,297 | B2 * | 7/2014 | Bromander | G06F 19/3406 600/427 |
| 8,793,618 | B2 | 7/2014 | Martin et al. | |
| 8,953,861 | B2 * | 2/2015 | Couch | 382/131 |
| 8,958,617 | B2 * | 2/2015 | Couch | A61B 6/032 382/131 |
| 8,966,385 | B2 | 2/2015 | Sako et al. | |
| 8,983,025 | B2 * | 3/2015 | Hirokawa | A61B 6/032 378/15 |
| D730,918 | S | 6/2015 | Park et al. | |
| 9,044,197 | B2 * | 6/2015 | Richard | A61B 6/544 |
| 9,069,081 | B2 * | 6/2015 | Campbell | G01T 1/026 |
| 9,129,044 | B2 * | 9/2015 | Shih | G06F 19/321 |
| 9,138,197 | B2 * | 9/2015 | Vaillant | A61B 6/4441 |
| 9,168,010 | B2 * | 10/2015 | Kazama | A61B 6/10 |
| D742,396 | S | 11/2015 | Li et al. | |
| D742,908 | S | 11/2015 | Lee et al. | |
| 9,220,568 | B2 | 12/2015 | Bromander et al. | |
| 9,262,444 | B2 | 2/2016 | Gross et al. | |
| D751,592 | S | 3/2016 | Link | |
| 9,275,473 | B2 | 3/2016 | Hori | |
| 2002/0128807 | A1 | 9/2002 | Sakamoto et al. | |
| 2003/0098354 | A1 | 5/2003 | Steklenski et al. | |
| 2004/0122308 | A1 | 6/2004 | Ding | |
| 2004/0159803 | A1 | 8/2004 | Akselrod et al. | |
| 2004/0227097 | A1 | 11/2004 | Brabec et al. | |
| 2004/0268258 | A1 | 12/2004 | Lee et al. | |
| 2005/0061991 | A1 | 3/2005 | Griggs et al. | |
| 2005/0209888 | A1 | 9/2005 | Oowaki et al. | |
| 2006/0017009 | A1 | 1/2006 | Rink et al. | |
| 2006/0085407 | A1 | 4/2006 | Kaminaga et al. | |
| 2007/0071169 | A1 | 3/2007 | Yeo et al. | |
| 2007/0114445 | A1 | 5/2007 | Schell et al. | |
| 2007/0129593 | A1 | 6/2007 | Gueye et al. | |
| 2007/0162855 | A1 | 7/2007 | Hawk et al. | |
| 2007/0185739 | A1 | 8/2007 | Ober et al. | |
| 2007/0221864 | A1 | 9/2007 | Neuhaus-Steinmetz et al. | |
| 2007/0241289 | A1 | 10/2007 | Fung et al. | |
| 2008/0098333 | A1 | 4/2008 | Champion et al. | |
| 2008/0292055 | A1 | 11/2008 | Boone | |
| 2009/0003527 | A1 | 1/2009 | Hoornaert et al. | |
| 2009/0045352 | A1 | 2/2009 | Morita | |
| 2009/0090865 | A1 | 4/2009 | Lub et al. | |
| 2009/0161818 | A1 | 6/2009 | Sakurai et al. | |
| 2009/0224176 | A1 | 9/2009 | Patel | |
| 2010/0099985 | A1 | 4/2010 | Gueye et al. | |
| 2010/0104159 | A1 | 4/2010 | Hirokawa et al. | |
| 2010/0239069 | A1 | 9/2010 | Bourdeaux et al. | |
| 2011/0036988 | A1 | 2/2011 | Campbell et al. |

(56) References Cited

U.S. PATENT DOCUMENTS

| | | |
|---|---|---|
| 2011/0078050 A1 | 3/2011 | Schwartz |
| 2011/0144658 A1 | 6/2011 | Wenderow et al. |
| 2011/0152882 A1 | 6/2011 | Wenderow et al. |
| 2011/0260070 A1 | 10/2011 | Polishchuk |
| 2012/0080602 A1 | 4/2012 | Garcia Diego et al. |
| 2012/0106817 A1 | 5/2012 | Shih et al. |
| 2012/0128116 A1 | 5/2012 | Sabol et al. |
| 2012/0148132 A1 | 6/2012 | Couch et al. |
| 2012/0150505 A1 | 6/2012 | Couch et al. |
| 2012/0150520 A1 | 6/2012 | Vaillant et al. |
| 2012/0179032 A1 | 7/2012 | Bromander et al. |
| 2012/0183122 A1 | 7/2012 | Ruijters et al. |
| 2013/0020508 A1 | 1/2013 | Kearfott |
| 2014/0140477 A1 | 5/2014 | Richard et al. |

FOREIGN PATENT DOCUMENTS

| | | |
|---|---|---|
| WO | WO 97/14017 | 4/1997 |
| WO | WO 97/32630 | 9/1997 |
| WO | WO 2005/119295 | 12/2005 |
| WO | WO 2008/006198 | 1/2008 |
| WO | WO 2009/111060 | 9/2009 |
| WO | WO 2011/137374 | 11/2011 |
| WO | WO 2012/051499 | 4/2012 |
| WO | WO 2012/071148 | 5/2012 |
| WO | WO 2012/075577 | 6/2012 |

OTHER PUBLICATIONS

Boer et al. "Real-Time Quantification and Display of Skin Radiation During Coronary Angiography and Intervention", American Heart Association, vol. No. 104, pp. 1779-1784, 2001.

Khodadadegan et al. "Automatic Monitoring of Localized Skin Dose with Fluoroscopic and Interventional Procedures", Journal of Digital Imaging, vol. No. 24, Issue No. 04, pp. 626-639, Aug. 2011.

Johnson et al. "Skin Dose Mapping for Fluoroscopically Guided Interventions", American Association Physics Medicine, vol. No. 38, Issue No. 10, pp. 5490-5499, Oct. 2011.

* cited by examiner

SYSTEM AND METHOD FOR USE IN MAPPING A RADIATION DOSE APPLIED IN AN ANGIOGRAPHY IMAGING PROCEDURE OF A PATIENT

TECHNICAL FIELD

The subject herein generally relates to a system and method to track ionizing radiation (e.g., x-rays), and more specifically to a system and method to manage direction of ionizing radiation dose toward an exposed subject.

BACKGROUND

The statements in this section merely provide background information related to the disclosure and may not constitute prior art.

Employment of the use of ionizing radiation (e.g., x-ray) is well known in the therapy or image acquisition of an exposed subject. Fields of application of ionizing radiation is common in the medical field (e.g., fluoroscopic, computed tomography (CT), x-ray, ablation of tissue, etc.) and security screening (e.g., airport baggage inspection). For example, radiological image acquisition generally includes directing a stream of ionizing radiation at the exposed subject, and measuring the attenuation of the ionizing radiation passing there through.

One concern with use of ionizing radiation includes an increased likelihood of harm or injury associated with radiation-induced injury to the tissue of the exposed subject. These deterministic risks can include skin reddening, rashes, burns, or hair loss. In fact, use of ionizing radiation is well-known in chemo-therapy or the ablation of diseased tissue. A variable that affects a likelihood of causing radiation-induced injury to tissue of an exposed subject includes a dose of radiation absorbed by the exposed subject. Variables that affect a dose of radiation absorbed by the exposed subject include a rate of delivery of radiation to the exposed subject, a time of exposure of radiation to the exposed subject, a fraction of radiation absorbed by the exposed subject, age or other characteristics of the exposed subject, and a location of exposure of radiation to the exposed subject. Another concern with use of ionizing radiation includes an increased likelihood of causing stochastic effects (e.g., radiation-induced cancers) to the exposed subject.

BRIEF SUMMARY

In view of the above concerns associated with use of ionizing radiation, there is a need for systems, methods and computer program products improved access to improve the knowledge to manage direction of radiation dose toward the exposed subject (e.g., patient) for different applications (e.g., fluoroscopic imaging, x-ray imaging, CT imaging of various exposed areas (e.g., chest, arms, legs, etc.) of an exposed subject). The above-described needs are addressed by the embodiments of the subject matter described herein.

One aspect of the subject matter includes a method of mapping a radiation dose applied in an angiography imaging procedure of a patient resting on a table, the method comprising the steps of: calculating with a computer processor an angulation of a radiation beam applied by an image acquisition system to the patient in the angiography imaging procedure relative to a table in response to a digital signal from the image acquisition system; calculating with a computer processor an angulation of the table relative to the room coordinate system; calculating an orientation of the patient resting on the table relative to the room coordinate system; calculating with a computer processor an intersection of the radiation beam relative to a two-dimensional cumulative dose two-dimensional map of pre-defined areas at a surface of the table; calculating with a computer processor the radiation dose applied by the image acquisition system at the intersection of the radiation beam to each of the predefined areas of the two-dimensional grid; and creating a graphic display with the computer processor mapping an aggregation of the radiation dose applied to each of the predefined areas of the two-dimensional grid relative to the patient resting on the table.

According to another aspect, a system for use in mapping a radiation dose applied in an angiography imaging procedure of a patient is provided. The system can include an image acquisition system that generates a radiation beam in the diagnostic image acquisition of the patient, the image acquisition system defined by an image acquisition system coordinate system. The system can further include a table having a surface in support of the patient during the angiography imaging procedure with the image acquisition system, the table defined by a table coordinate system having a predefined orientation to a room coordinate system. The system can further include a computer processor in communication to execute a plurality of programming instructions stored in a memory, the plurality of programming instructions to instruct the computer processor to perform the steps of: calculating an angulation of the radiation beam applied by the image acquisition system to the patient in the angiography imaging procedure relative to the table; calculating an angulation of the table relative to the room coordinate system; calculating with a computer processor an intersection of the radiation beam relative to a two-dimensional grid of pre-defined areas at the surface of the table; calculating with a computer processor the radiation dose applied by the image acquisition system at the intersection of the radiation beam to each of the predefined areas of the two-dimensional grid; calculating with a computer processor an orientation of the patient relative to the two-dimensional grid of predefined areas; and creating a graphic display with the computer processor illustrative of an aggregation of the radiation dose applied to each of the predefined areas of the two-dimensional grid and the orientation of the patient for viewing by a user.

According to yet another aspect, a non-transitory computer program product having a plurality of modules of program instructions for execution by a computer processor in determining a radiation dose applied by radiation beam emitted from an image acquisition system in a diagnostic imaging scan of a patient resting on a table is provided. The computer program product can include a module to calculate an angulation of the radiation beam applied by the image acquisition system to the patient in the diagnostic imaging scan relative to a table coordinate system; a module to calculate an angulation of the table relative to an image acquisition system coordinate system; a module to calculate an intersection of the radiation beam relative to a two-dimensional grid of pre-defined areas at the table; a module to calculate the radiation dose applied by the image acquisition system at the intersection of the radiation beam to each of the predefined areas of the two-dimensional grid; a module to calculate an orientation of the patient relative to the two-dimensional grid of predefined areas; and a module to create a graphic display illustrative of an aggregation of the radiation dose applied to each of the predefined areas of the two-dimensional grid for viewing by a user.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. The term user and/or the plural form of this term is used to generally refer to those persons capable of accessing, using, or benefiting from the present disclosure. As used herein, when the phrase "at least" is used, it is open-ended in the same manner as the term "comprising" is open-ended.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
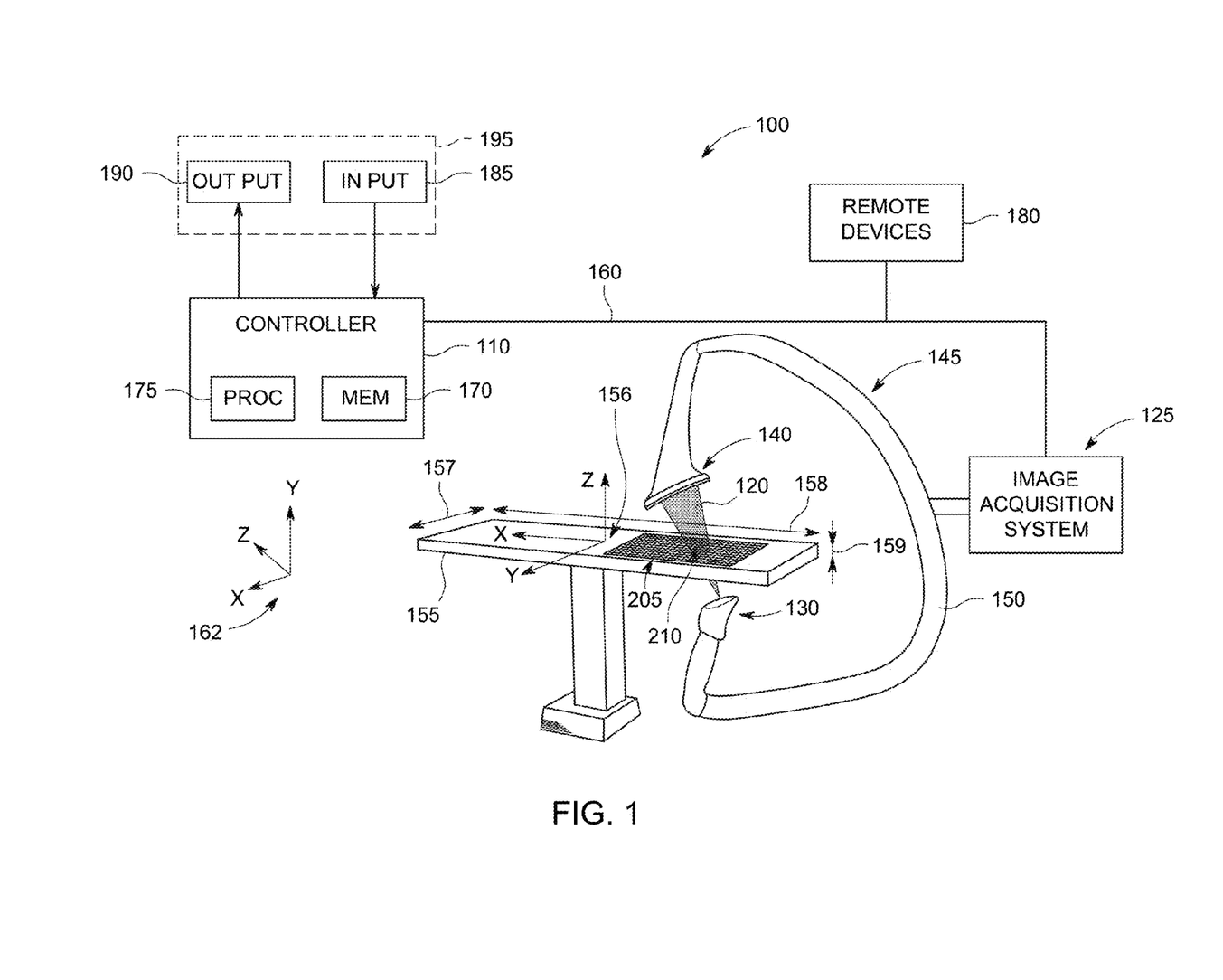
FIG. 1 shows a schematic block diagram of an example of a system in accordance to the subject matter described herein.
Figure 3:
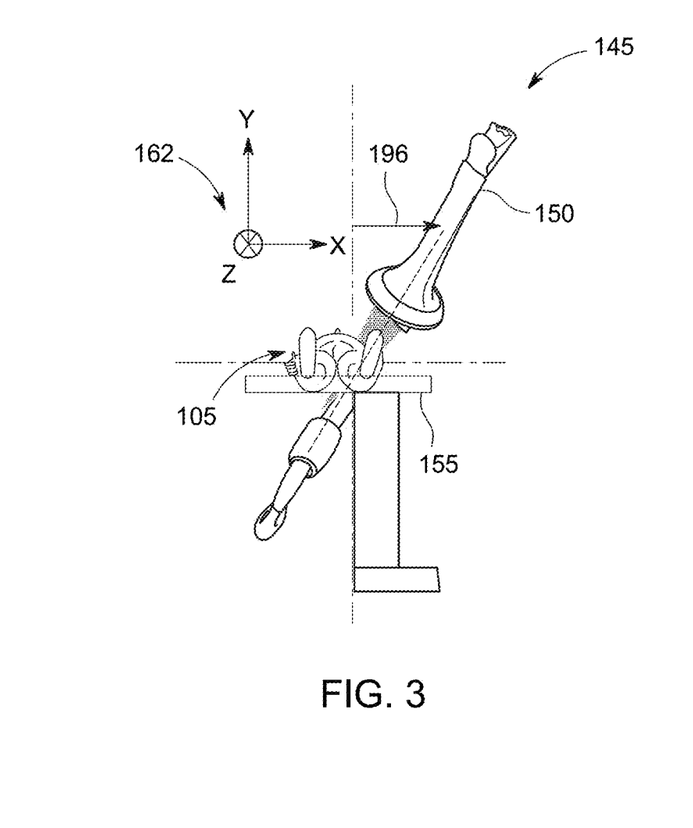
FIG. 3 shows another detailed illustration of a first angulation of the radiation beam measured by the system of FIG. 1 in accordance with the subject matter described herein.
Figure 4:
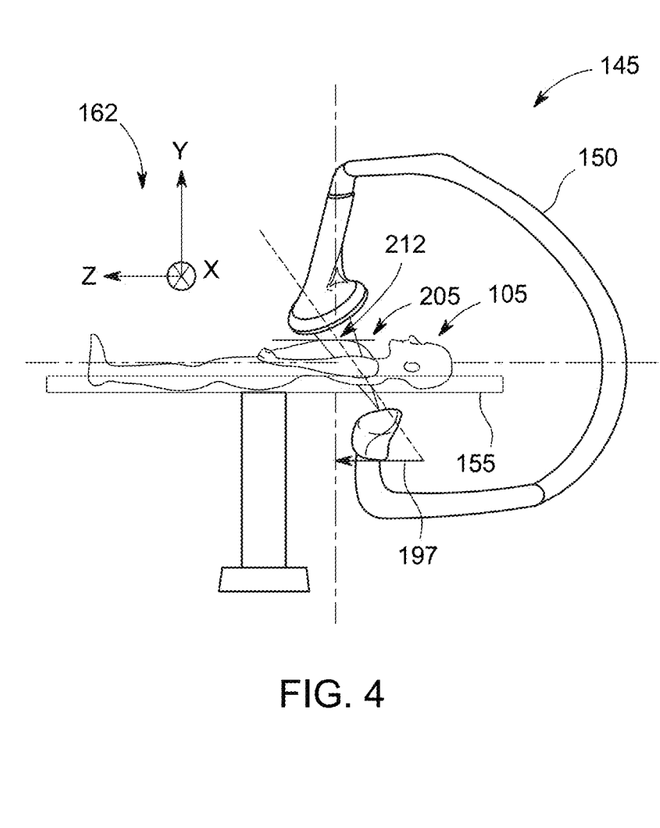
FIG. 4 shows another detailed illustration of an another angulation of the radiation beam measured by the system of FIG. 1 in accordance with the subject matter described herein.

FIG. 1 illustrates one embodiment of a system 100 to track and report delivery of radiation dose during or in an image acquisition procedure or other protocol involving direction of ionizing radiation dose toward an exposed subject 105 (See FIGS. 3 and 4). The system 100 can generally include a controller 110 in communication via a network connection 160 with an ionizing radiation beam 120 generating or emitting ionizing radiation which is collected by an image acquisition system 125 in accordance to the subject matter described herein.

One example of the type of image acquisition system 125 can be an angiographic imaging system, computed tomography (CT), a fluoroscopic imaging system, etc. having the radiation source 130 projecting the ionizing radiation beam (e.g., x-rays) 120 through the exposed subject 105 to be received at a detector 140 in a conventional manner. The ionizing radiation beam 120 can be attenuated with passing through exposed subject 105, until impinging upon the detector 140. The detector 140 can translate the attenuation of ionizing radiation beam 120 to generate the image or image frames illustrative of a region of interest of the exposed subject 105.

The illustrated example of the image acquisition system 125 can generally include a gantry 145 comprising an arm 150 that can rotate in at least two dimensions of space around the patient 105. The arm 150 can be generally C-shaped and in support of the radiation source 130 at one of its ends and the detector 140 at the other of its ends. Yet, the shape of the arm 150 can be curvilinear, angular, circular or O-shaped, etc. and is not limiting on the subject matter described herein. The radiation source 130 and detector 140 can be mounted at the opposite ends of the arm 150 such that, with the exposed subject 105 (See FIGS. 3 and 4) interposed there between, that the ionizing radiation beam 120 emitted can be incidental to and detected by the detector 140. The detector 140 can be connected to a lift (not shown) used to raise and lower the detector 140 in the direction of emission. The patient 105 is irradiated by ionizing radiation beam 120, and the detector 140 produces image data representing characteristics of the interposed patient 105 that can be conventionally displayed on the monitor (not shown) of the image acquisition system 125 and stored electronically.

Figure 2:
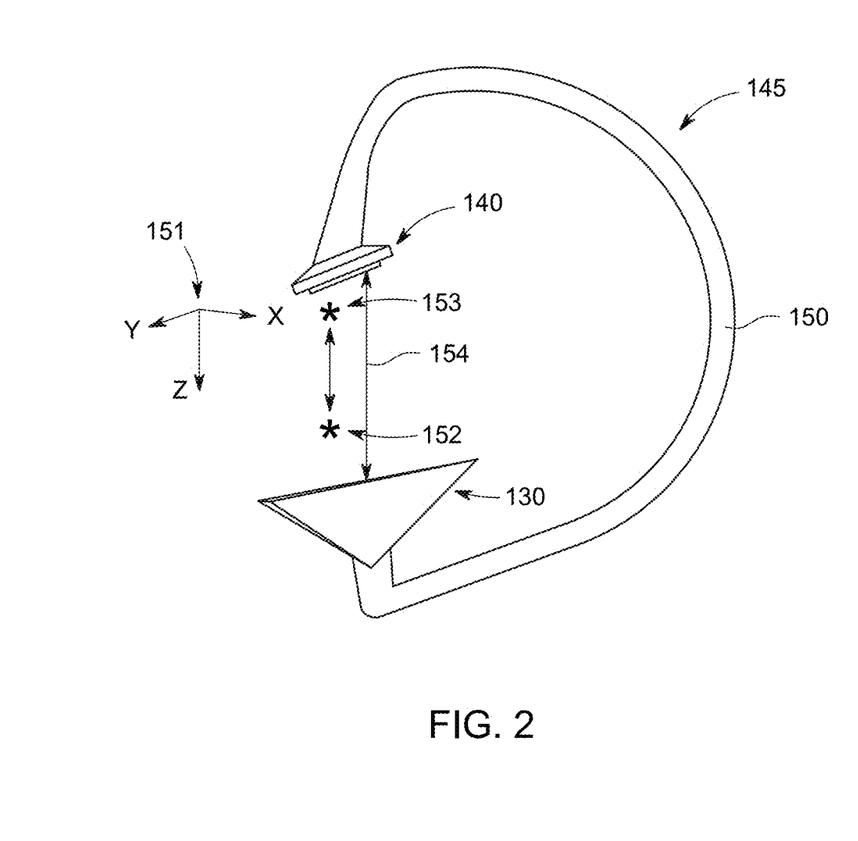
FIG. 2 shows a detailed illustration of a C-arm of the image acquisition system of FIG. 1 in accordance with the subject matter described herein.

Referring to FIGS. 1 and 2, the image acquisition system 125 can be defined by an image acquisition or gantry coordinate system 151 (e.g., rectangular, polar, etc.) that defines a reference point 152 and an isocenter 153 of the radiation source 130 and detector 140. By defining the reference point 152 and isocenter 153 relative to the image acquisition or gantry coordinate system 151, the system 100 can calculate a distance (d_icrp) between the isocenter 153 and the reference point 152, a distance (d_sic) between the radiation source 130 to the isocenter 153, a distance (d_sd) 154 between the source radiation 130 and the detector 140.

Referring back to FIG. 1, the gantry 145 can be operated to move in combination with a table 155 on which the patient 105 reclines. The table 155 can be defined by a table coordinate system 156, a width 157, a length 158, and a thickness 159 (which may or may not include a mattress (not shown) defined to have a mattress length, width and thickness).

The image acquisition system 125 can include its own control unit (not shown) to automatically control the drive (not shown) to move the gantry 145 or the table 155 or combination thereof in combination with controlling the intensity, duration, and shape of the ionizing radiation beam 120 in performing an angiography procedure. The ionizing radiation beam 120 can be attenuated as it passes through the exposed subject 105, until impinging upon the detector 140, generating the image or image frames (not shown) illustrative of a region of interest of the exposed subject 105. The acquired image or sequence of acquired image frames can be digitized and communicated recording and storage. The control unit can be further to perform image processing on the acquired image data for illustration to the user.

The controller 110 can be connected in communication via a network connection 160 to the image acquisition system 125. Although the controller 110 can be located remote from the image acquisition system 125, it should be understood that the controller 110 can otherwise be located integrated with or adjacent to the image acquisition system 125 and is not limiting on the subject matter described herein.

The controller 110 can generally operate to receive, process, and convey information to and from the image acquisition system 125. For example, the controller 110 can operate to receive and process information of the movement, position, or orientation of the image acquisition system 125 or gantry 145 or arm 150 relative the exposed subject 105. To perform this task, the system 100 can include predefined data or receive input that defines the image acquisition or gantry coordinate system 151 of FIG. 2 relative to the table coordinate system 156 relative to a third or defined space coordinate system 162. As illustrated in FIGS. 3-6, the table 155 can be angled in combination with the varied orientation of the gantry 145 to capture various angles of image acquisition in all three-dimensions of the patient 105 relative to the ionizing radiation beam 120. Calculating or defining the spatial orientation of the coordinate systems 151, 156, and 162 relative to one another in combination with receiving input of parameters of the orientation of the image acquisition system 125, table 155 and imaged subject 105 enables the system 100 to calculate in three-dimensional space the intersection of the ionizing radiation beam 120 relative to the image subject 105.

The example of the controller 110 can generally include a memory 170 having a series of computer readable program instructions for execution by a computer or hardware processor (herein "computer processor") 175. The example memory 170 can include or be a tangible, computer program product of varying type generally operable to store electronic formatted data or information and program instructions accessible and readable by the computer or hardware processor 175. In certain examples, the memory 170 can be accessible by an external computing device (not shown) via the network connection 160.

The computer-readable instructions can comprise a programming code for execution by the computer or hardware processor 175. The programming code can be embodied in software stored on the memory 170 independent of or in combination with software embodied in firmware or dedicated hardware. The computer program product can include a computer-readable storage medium that is tangible, non-transitory, and having volatile and non-volatile, and removable and non-removable media for storage of electronic-formatted information such as computer readable program instructions or modules of instructions, data, etc. that may be stand-alone or as part of the controller 110. As used herein, the term tangible, non-transitory computer readable storage medium can be expressly defined to include any type of computer readable storage device and/or storage disk and to exclude propagating signal media and to exclude transmission media. As used herein, "tangible computer readable storage medium" and "tangible machine readable storage medium" can be used interchangeably.

Examples of the memory 170 can include, but are not limited to, random access memory (RAM), read only memory (ROM), Synchronous Dynamic Random Access Memory (SDRAM), Dynamic Random Access Memory (DRAM), EEPROM, flash memory, a cache, compact disc (CD), digital versatile disc (DVD) or other optical storage, magnetic cassettes, magnetic tape, magnetic disk storage or other magnetic storage devices, a hard drive, a flash memory, or any other medium which can be used to store the desired electronic format of information or program instructions for a duration and which can be accessed by the computer or hardware processor 175 or at least a portion of the controller 110.

The example computer or hardware processor 175 can include hardware to execute one or more tasks as defined by the computer readable program instructions. The computer or hardware processor 175 can be, for example, part of a computer server, a laptop or desktop, a mobile device (e.g., a cell phone, a smart phone, a tablet such as an IPAD™), a personal digital assistant (PDA), an Internet appliance, or any other type of computing device. For example, the computer or hardware processor 175 can be implemented by one or more integrated circuits, logic circuits, microprocessors or controllers from any desired family or manufacturer.

The memory 170 and computer or hardware processor 175 as referred to herein can be stand-alone or integrally constructed as part of various programmable computing devices of various types, including for example a cache, a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like and any combination thereof operable to execute the instructions associated with implementing the method (discussed later) of the subject matter described herein.

The system 100 can be configured to communicate generated or created displays to miscellaneous remote computing devices 180 as referenced herein can include: a mobile telephone; a computer such as a desktop or laptop type; a Personal Digital Assistant (PDA) or mobile phone; a notebook, tablet or other mobile computing device; or the like and any combination thereof. The subject matter of this description may be implemented as the above-described stand-alone computer program product or for execution as an application capable of execution by one or more remote computing devices 180. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the remote computing device(s) 180.

The network connection 160 can facilitate transmission of electronic or digital data within and/or among the system 100. The example network connection 160 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN); a local area network (LAN); the Internet; a cloud-based computing infrastructure of computers, routers, servers, gateways, etc.; or any combination thereof associated therewith that allows the system 100 or portion thereof to communicate with the image acquisition system 125 and various remote computing devices 180 described above. With respect to the example of the network connection 160 as including a cloud-based infrastructure, the system 100 can share information via web-based applications, cloud storage and cloud services. For example, a Web-based portal may be used to facilitate access to information, etc. The system 100 can illustrate the Web-based portal as a central interface to access information and applications, and data may be viewed through the Web-based portal or viewer, for example. Additionally, data may be manipulated and propagated using the Web-based portal, for example. The Web-based portal can be accessible locally (e.g., in an office) and/or remotely (e.g., via the Internet and/or other network or connection), for example.

The controller 110 can also be in communication with an input device 185 and an output device 190. Examples of the input device 185 include a keyboard, joystick, mouse device, touch-screen, pedal assemblies, track ball, light wand, voice control, or similar known input device known in the art. Examples of the output device 190 include a liquid-crystal monitor, a plasma screen, a cathode ray tube monitor, a touch-screen, a printer, audible devices, etc. The input device 185 and output device 190 can be in combination with the image acquisition system 125, an independent of one another, or combination thereof as an interface 195 to the system 100.

Having provided an example of one construction of the system 100 as shown in FIG. 1 in accordance with above-description as well as various displays (see FIGS. 2-4) generated by the system 100, the following is a description of an example of a method to operate the system 100 in accordance with the subject matter described herein. It should also be understood that the sequence of the acts or steps of the method as discussed in the foregoing description can vary. Also, it should be understood that the method may not require each act or step in the foregoing description, or may include additional acts or steps not disclosed herein. It should also be understood that one or more of the steps of the method can be represented by one or more computer program modules of computer-readable program instructions stored in the memory 170 of the system 100. As mentioned above, the method can be implemented using coded instructions (e.g., computer and/or machine readable instructions). The terms module and component as referenced herein can generally represent program code or instructions that causes specified tasks when executed on the computer or hardware processor 175. The program code can be stored in one or more computer readable mediums that comprise the memory 170.

Assume for sake of example, assume that an exposed subject 105 is a patient and the image acquisition system 125 is operable to perform an angiography imaging procedure on the exposed subject 105. As described above, the image acquisition system 125 can be operable to move the orientation of the gantry 145 and mounted radiation source 130 and detector 140 in combination with moving the orientation of the table 155 in support of the exposed subject 105 to be located in a desired orientation between the radiation source 130 and detector 140 to capture the desired orientation of image data of the respective area of interest. Also for sake of example, assume the system 100 receives or otherwise has stored predefined or input data of the coordinate systems 151, 156 and 162 relative to one another in addition to input parameters of the table 155 and isocenter 153 or reference point 152 of the gantry 145.

With receiving input data of the location of the position of the gantry 145 or image acquisition system (e.g., the position of the isocenter 153 or reference point 152 in the coordinate system 151) 125, the system 100 can calculate a position angle or angulation of the axis of image acquisition (as defined by the axial alignment of the radiation source 130 and detector 140 relative to one another in the space coordinate system 162) from the point of view of the exposed subject 105.

FIGS. 3 and 4 illustrate, based on received data, an example of calculating a positioner angle of the image acquisition as defined by the angulation of the gantry 145 relative to the coordinate system 162. With predefined information or input of the relation of the coordinate systems 151 156, 162 to one another, the system 100 can calculate angulation of the gantry 145 relative to the exposed subject 105 relative to the space coordinate system 162. The calculated angulation of the gantry 145 can include measure of a positioner primary angle "alpha 1) 196 (See FIG. 3) defined by a position of the ionizing radiation beam 120 about the exposed subject 105 from the right anterior oblique (RAO) view to left anterior oblique (LAO) view direction where movement from RAO view to vertical is positive as understood to those skilled in angiographic imaging; and positioner secondary angle "alpha2" 197 (See FIG. 4) defined by a position of the ionizing radiation beam 120 about the exposed subject 105 from the caudal to cranial direction where movement from caudal to vertical is positive as understood to those skilled in angiographic imaging.

Figure 5:
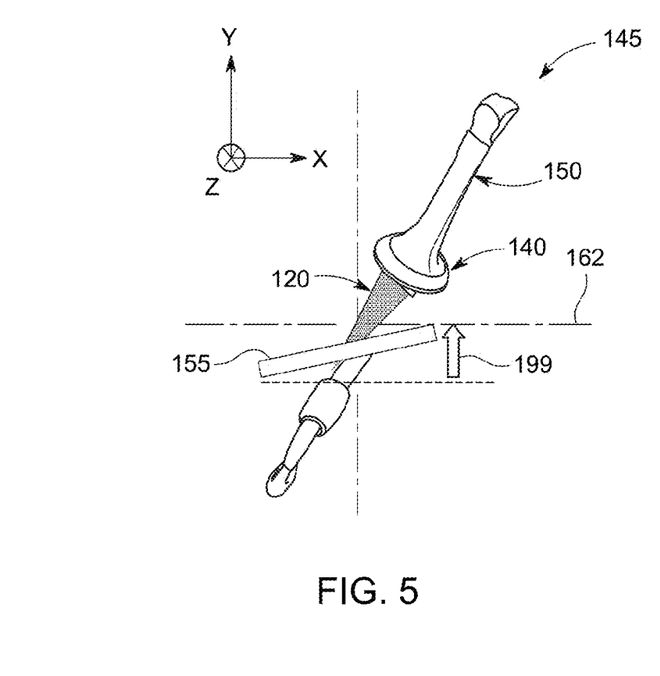
FIG. 5 illustrates detailed illustration of an angulation of the table measured by the system of FIG. 1 in accordance to the subject matter described herein.
Figure 6:
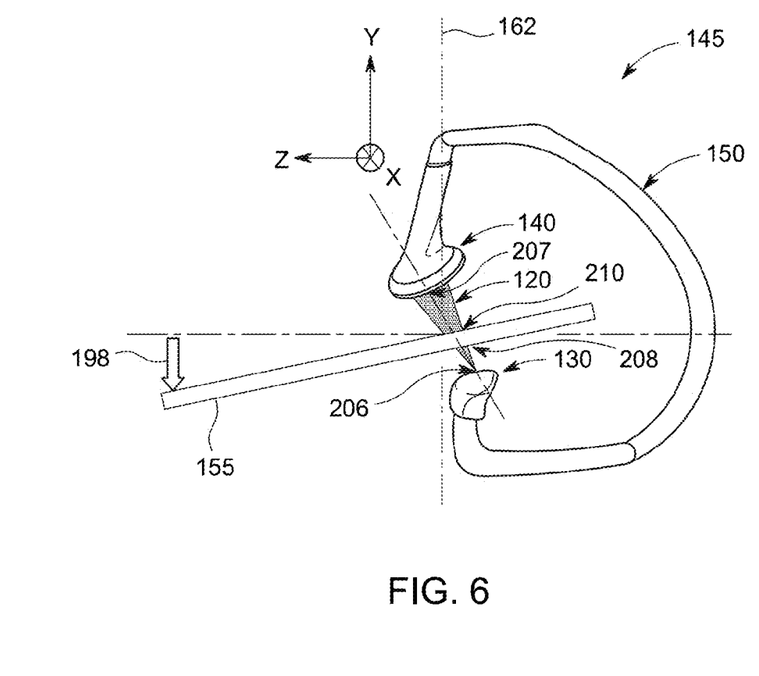
FIG. 6 shows another detailed illustration of an angulation of the table measured by the system of FIG. 1 in accordance to the subject matter described herein.
Figure 7:
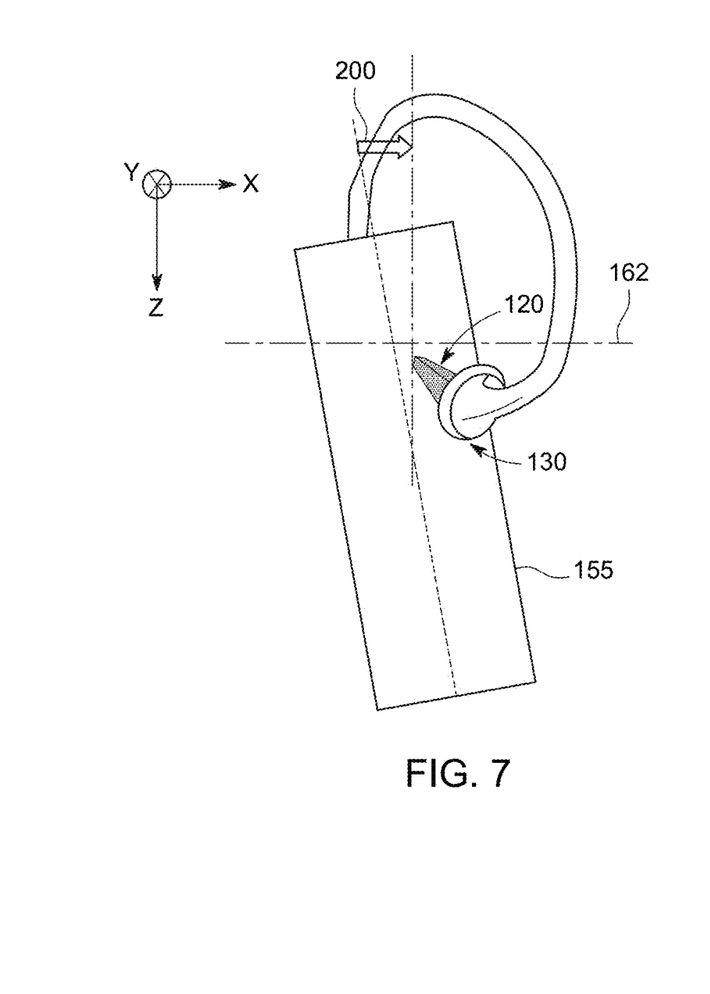
FIG. 7 shows another detailed illustration of an angulation of the table measured by the system of FIG. 1 in accordance to the subject matter described herein.

FIGS. 5-7 illustrate, based on received data, an example of calculating an orientation (e.g., angulation, spatial relation) of the table 155 relative to the space coordinate system 162. With the above-acquired information, the system 100 can calculate table head tilt angle 198 (See FIG. 6), table cradle tilt angle 199 (See FIG. 5), and a table horizontal rotation angle 200 (See FIG. 7) of the table 155 relative to the space coordinate system 162. The system 100 can also receive further input of the relationship of the orientation of the exposed subject 105 relative to the table 155 and table coordinate system 156 and surface irradiated under the table 208. This information directed to orientation of the exposed subject 105 can be received from the acquired image file associated with the image acquisition of the exposed subject 105. With the above-described information, the system 100 can calculate the angular relation and coordinates of the radiation source 130 and detector 140 mounted on the arm 150 of the image acquisition system 125 from the point of view of the exposed subject 105.

With the above-described calculated parameters, the system 100 can include computer program instructions for execution by the computer or hardware processor 175 to calculate the dose of radiation applied at the calculated R(U, theta) represents rotation of the unit vector position of intersection 210 at a two-dimensional grid 205 of defined areas with respect to the table 155. The illustrated example of the two-dimensional grid 205 is generally quadrilateral shaped (e.g., square) comprised of a ten-by-ten layout of defined areas (also squares). Yet the number and shape of the defined areas that comprise the two-dimensional grid 205 can vary.

Assume that (Ui) is a unit vector in the direction (x, y, z) respectively of the space coordinate system 162, and that (Ui) is through the angle (theta). Referring to FIG. 6, the location (e.g., coordinates) 206 of the radiation source 130 ("S") with respect to the space coordinate system 162 can calculated according to:

$$S = R(R(Uz, -Alpha1) * Ux, -Alpha2) * R(Uz, -Alpha1) * \begin{pmatrix} 0 \\ -d_{sic} \\ 0 \end{pmatrix}$$

The location of the reference point ("RP") 152 with respect to the space coordinate system 162 can be calculated according to:

$$RP = R(R(Uz, -Alpha1) * Ux, -Alpha2) * R(Uz, -Alpha1)) * \begin{pmatrix} 0 \\ -d_{icrp} \\ 0 \end{pmatrix}$$

The location of the detector ("D") with respect to the space coordinate system 162 can be calculated according to:

$$D = R(R(Uz, -Alpha1) * Ux, -Alpha2) * R(Uz, -Alpha1) * \begin{pmatrix} 0 \\ d_{sd} - d_{sic} \\ 0 \end{pmatrix}$$

The location of the four corners of the ionizing radiation beam 120 at the detector 140 can be calculated according to the following:

$$Bi = R(R(Uz - Alpha1) * Ux - Alpha2) * R(Uz - Alpha1) * \begin{pmatrix} \pm \frac{\sqrt{CFA}}{2} \\ d_{sd} - d_{sic} \\ \pm \frac{\sqrt{CFA}}{2} \end{pmatrix}$$

where (i) ranges between 1 to 4 and assuming oriented of the gantry 145 so that a plane of the arm 150 has an axis of reflection symmetrical with respect to a surface of the detector 140, and assuming that the ionizing radiation beam 120 meets the surface of the detector 140 in the middle of two opposite sides and that an area (e.g., assume a square shape, but can be any shape) delimiting a radiation collimated field.

In general, the ionizing radiation beam 120 can be uniquely identified by its incidence point ("I") 207 at the plane of the detector 140 with respect to the space coordinate system 162 according to:

$$I = R(R(Uz, -Alpha1) * (Ux, -Alpha2) * R(Uz, -Alpha1) * \begin{pmatrix} x \\ d_{sd} - d_{sic} \\ z \end{pmatrix}$$

where (x) and (y_) define to the irradiated surface on the plane of the detector 140 (e.g., x in $$\left[ -\frac{\sqrt{CFA}}{2}, +\frac{\sqrt{CFA}}{2}, z \text{ in } \left[ -\frac{\sqrt{CFA}}{2}, +\frac{\sqrt{CFA}}{2} \right] \right]$$

in the square case).

The location of the table 155 with respect to the space coordinate system 162 can be defined as a combination of two translations from the isocenter 153: a first translation (T0) that transforms the isocenter 153 into the table 155 home position, and a second translation (Ttrans) that takes into account movement of the table 155 (e.g., position information from DICOM file directed to table latitude, longitude, and height) during the image acquisition procedure. In addition, the method includes calculating a linear transform that takes into account rotation of the table 155 (cradle angulation, head angulation and rotational angulation)

$$T(W) = T0 - Ttrans + R(R(Uz, -Gamma2)R(Ux, -Gamma1)Uy, -Gamma3) * R(R(Uz, -Gamma2) * Ux, -Gamma1) * R(Uz, -Gamma2)W$$

where (W) can be a vector that defines a location of a given point in the table coordinate system 156. The above-described formula is an example based degrees of freedom of movement of the table 155 and is not limiting. In another example, where the angulation of the table 155 about y-axis is independent of the angulations on x and z axis, the following formula can utilized:

$$T(W) = T0 - Ttrans + R(Uy, -Gamma3) * R(R(Uz, -Gamma2) * Ux, -Gamma1) * R(Uz, -Gamma2)W$$

The table coordinate system 156 can be Cartesian and coincide with the space coordinate system 162 at the angulation of the table 155 so as to be set to 0 and where the center of the table 155 can be defined to be at the isocenter 153. Accordingly, the four corners that can define the table 155 can be calculated according to:

$$Wc = \begin{pmatrix} \pm \text{Width}/2 \\ 0 \\ \pm \text{Length}/2 \end{pmatrix}$$

which corresponds with respect to the space coordinate system 162 to be: Tc=T(Wc).

Assuming (Wi) to be a location of the set of points of incidence of an intersection 210 of the corners (Wc) of the ionizing radiation beam 120 extending linearly from the radiation source 130 at the two-dimensional grid 205 of the table 155, one can calculate the areas (e.g. squares or bins comprising the two-dimensional grid 205) of intersection 210 at the two-dimensional grid 205 that are irradiated as follows:

$$Wi = \begin{pmatrix} x_i \\ y_i = 0 \\ z_i \end{pmatrix}$$

One can calculate M (x,y,z) as a point of the ionizing radiation beam 120 originating from the radiation source (S) 130 that meets the incident point (I) 207 of the detector 140 according to:

$$M = k*(I-S)/\|(I-S)\|$$

where k is a distance between (M) and the location 206 of the radiation source (S) 130.

The point (M) according to coordinates (Wi) with respect to the table coordinate system 156 can be calculated with respect to the space coordinate system 162 as follows:

$$M=T(W)$$

As a result, for any point located with the respect to the table coordinate system 156, one can uniquely calculate (k) and (I) with respect to the space coordinate system 162, and (M) and (W) can represent the same point on different coordinate systems 156 and 162.

For example, if (I) 207 coincides with (Bi) and assuming a solution for (M) that has a set of coordinates (W) for intersection 210 with respect to the table coordinate system 156 of shape according to:

$$W = \begin{pmatrix} x \\ y=0 \\ z \end{pmatrix},$$

the resulting location (x, z) for each (Bi) gives a corner of the irradiated quadrilateral surface (assuming square-shape of ionizing radiation beam 120). However, the shape of the ionizing radiation beam 120 and resultant intersection 210 can vary and is not limiting on the subject matter. With the location (W) of the irradiated surface of the table 155 with the respect to the table coordinate system 156, the irradiated sectors of the two-dimensional grid 205 can be calculated. Using the method described above, one can also calculate a solution (M) of coordinates W=(x, y, z) where x, y, and z represent the location of intersection 210 of the ionizing radiation beam 120 at the exposed subject 105 (i.e., patient's skin), where using an embodiment of the two-dimensional grid 205 deformed to the contour of the exposed subject 105.

The method can further account for attenuation of the ionizing radiation beam 120 due to the table thickness (Tt) 159. If (Mb) is the location of the incident point 207 of the ionizing radiation beam 120 at the bottom-side (Wb) of the surface of the table 155 supporting the exposed subject 105, and (Mt) is the exit point of the ionizing radiation beam 120 from the top side (Wt) of the table 155, the apparent table thickness 159 can be calculated according to:

$$\|MbMt\|=\|WbWt\|$$

where Wb and Wt are known according to:

$$Wb = \begin{pmatrix} xb \\ yb=-\text{thickness} \\ zb \end{pmatrix}, \text{ and } Wt = \begin{pmatrix} xt \\ yt=0 \\ zt \end{pmatrix}$$

(Mb) and (Mt) can be calculated according to:

$$Mb=k^*(I-S)/\|(I-S)\| \text{ and } Mt=k'^*(I-S)/\|(I-S)\|.$$

where (Mb) and (Mt) can be uniquely solvable in (kb, xb, zb) and in (kt, xt, zt), assuming the ionizing radiation beam 120 is not parallel to the table 155.

An example of how the system 100 can calculate the dose of radiation applied at the point (Me) of incidence or intersection 210 of the ionizing radiation beam 120 at the exposed subject 105 can be calculated according to the following:

$$\text{Dose}=\text{Dose}(RP)^*(d\_sic-d\_icrp)2^*\exp(-mu^*WbWt)/k''2$$

where (mu) represents linear attenuation of the dose with respect to the table 155 based on the table material and (k")=‖SM‖. With receipt or predefining certain physical parameters (e.g., height, chest, waist, etc.) of the exposed subject 105, the above formulation to calculate dose can be projected to the location (Me) (see reference 212 in FIG. 4)) with respect to the deformed contour of the two-dimensional grid 205 or portion thereof at the surface of the desired landmark of interest of the exposed subject 105 (i.e., patient's skin surface (e.g., back surface, chest surface, etc.)). The system 100 can use the above formula to calculate the dose at the intersection 210 of the ionizing radiation beam 120 with the two-dimensional grid 205 located at various landmarks (e.g., mattress, exposed subject, table surface) by varying the respective coordinates of the landmarks (i.e., equate to Wt in formula above). The above calculation of dose is an example and not limiting on the subject matter described herein. In particular, the calculation of dose can further include mass energy coefficients, backscatter factors, etc.

The image acquisition system 125 can direct or deliver the ionizing radiation beam120 through the exposed subject 105. Assume for sake of example that the system 100 receives or collects data associated with either a real-time image acquisition procedure or a prior recorded performance of an image acquisition on the exposed subject 105. The acquired information can include a dose or dose rate of radiation (e.g., absorbed dose in Gray (Gy), cumulative air kerma with regards to fixed reference position with regards to the interventional reference point at a fixed distance from the isocenter 153 of the image acquisition system 125, equivalent dose in Sievert (Sv), effective dose relative to a tissue weighting factor, directed by the individual image acquisition system 125 in acquisition of images of the patient 105, a patient position relative to the image acquisition system 125 or radiation source 130, a distance between the radiation source 130 (e.g., x-ray tube assembly focal spot where the an electron beam hits the anode target) to the scintillator of the detector 140) (also referred to as source to image distance (SID)), a comparison of the directed dose relative to the acquired upper dose threshold, a measure of radiation dose directed per SID, a cumulative dose directed to the patient for each SID or SID grouping, details of the status information (e.g., acquisition mode, positioning of radiation source 130 and/or detector 140 in relation in time to direct radiation dose or cumulative dose, frame rate, auto exposure preference, detail level of image data, total number of runs or scans, total scan time or duration of image acquisition, details associated with calibration (e.g., calibration date, etc.) of the image acquisition system 125, and total radiation dose directed to the exposed subject 105).

For a prior recorded image acquisition event, an example of the image acquisition data can be retrieved from a Digital Imaging and Communication in Medicine (DICOM) image format associated with the exposed subject 105. The DICOM image file can generally combine medical image data (e.g., pixel values associated with image frames, etc.) with metadata (e.g., patient identifier and parameters, type of study, imaging modality identifier of equipment that acquired the medical imaging data, imaging series in addition to the image frames identifiers, medication or contrast agents given at time of procedure, etc. that together comprise an information object) in a known manner that creates a rich description of a performed medical imaging procedure in a ready accessible format.

With the above-described data received or calculated in either in real-time during the imaging procedure or following the imaging procedure, the method of operating the system 100 can include analyzing the acquired data or information to calculate and create the mapping of the ionizing radiation dose applied in an angiography imaging procedure of an exposes subject 105. The method can include calculating with the computer or hardware processor 175 the angulation of the ionizing radiation beam 120 applied by the image acquisition system 125 to the exposes subject 105 in the angiography imaging procedure relative to the table 155 and table coordinate system 156. The system 100 can also calculate with the computer or hardware processor 175 an orientation or angulation of the table 155 relative to the space coordinate system 162, as well as calculate an orientation of the exposed subject 105 resting on the table 155 relative to the space coordinate system 162. With data on the orientation of the table 155, the computer or hardware processor 175 can calculate the orientation of the exposed subject 105 relative to a two-dimensional grid 205 defined at the table 155. The orientation (e.g., angular coordinates) of the exposed subject 105 relative to the two-dimensional grid 205 can dependent on an orientation of the exposed subject 105 relative to the table coordinate system 156 or the space coordinate system 162, adjusted based on a modifier factor value for an orientation of the exposed subject 105 identified for the respective imaging procedure.

With calculation of the orientation (e.g., in angulation or grid coordinates relative to the coordinate systems 151, 156, 162) of the exposed subject 105 and the ionizing radiation beam 120, the system 100 can calculate with the computer or hardware processor 175 an intersection 210 of the ionizing radiation beam 120 relative to the two-dimensional grid 205 of pre-defined areas (e.g., squares) at the table 155 as shown in FIG. 1. The plane of the two-dimensional grid 205 can be generally aligned with the surface of the table 155, or offset therefrom a distance based on parameters of the exposed subject 105.

With information either received in the DICOM image file or in real-time from the image acquisition system 125, the system 100 can calculate with the computer or hardware processor 175 the cumulative radiation dose applied by the image acquisition system 125 at the intersection 210 of the ionizing radiation beam 120 to each of the predefined areas of the two-dimensional grid 205, and create a graphic display 400 (See FIG. 8) with the computer or hardware processor 175 mapping an aggregation of the cumulative radiation dose applied to each of the predefined areas of the two-dimensional grid 205 relative to the exposed subject 105 resting on the table 155 and the duration of the imaging procedure. The step of calculating with the computer or hardware processor 175 the cumulative radiation dose applied by the image acquisition system 125 at the intersection 210 of the ionizing radiation beam 120 to each of the predefined areas of the two-dimensional grid 205 need not be dependent on analysis of the pixel data in the DICOM image data file associated with the angiography procedure of the exposed subject 105. Rather, the system 100 can calculate the cumulative dose of radiation applied to each of the predefined areas of the two-dimensional grid 205 dependent on a plurality of parameters including: a table material, a table material density, a table thickness 159, a mattress thickness, a mattress material, and a mattress density, as well as other geometrical orientation of the image acquisition system 125 relative to the exposed subject 105 on the table 155 and operating parameters of the image acquisition system 125 in acquiring the image data as recorded in either the DICOM image file or communicated directly from the image acquisition system 125. The cumulative radiation dose applied by the image acquisition system 125 at the intersection 210 of the ionizing radiation beam 120 to each of the predefined areas of the two-dimensional grid 205 can further be dependent on a type of imaging event with the image acquisition system 125, wherein the type of imaging event is one of a fluoroscopic image acquisition, a stationary image acquisition, a stepping image acquisition, and a rotational image acquisition. The computer or hardware processor 175 of the system 100 in calculating the cumulative radiation dose applied by the image acquisition system 125 at the intersection 210 of the ionizing radiation beam 120 to each of the predefined areas of the two-dimensional grid 205 can be further dependent on a time of duration of the type of imaging event as defined in the recorded image file of the exposed subject 105.

Figure 8:
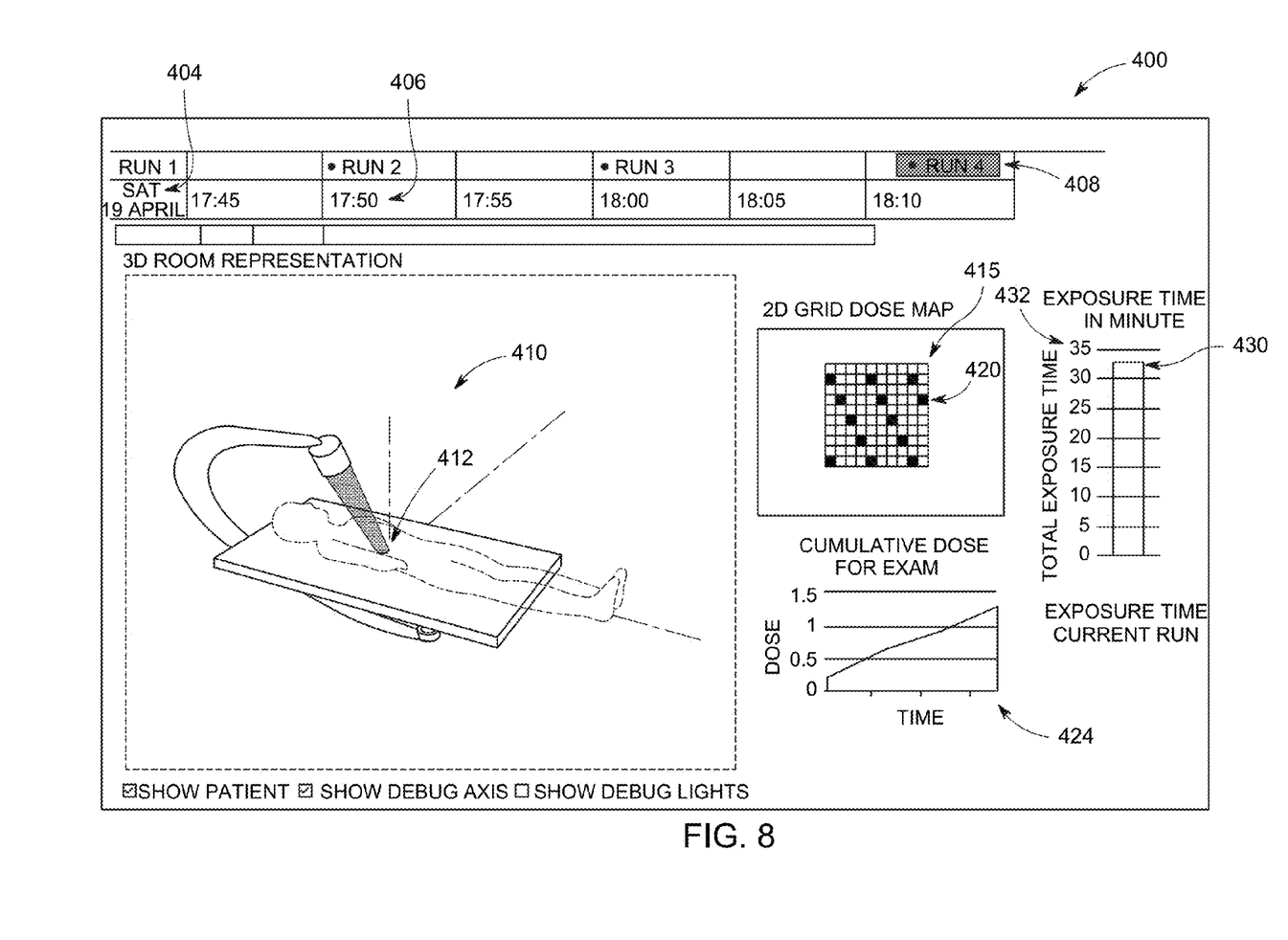
FIG. 8 shows an illustration of one example of a graphic user interface and output created by the system of FIG. 1 in accordance to the subject matter described herein.

Referring to FIG. 8, having analyzed the above-described data and calculated the intersection 210 and measure of the cumulative dose applied, the computer or hardware processor 175 can create a graphic display 400 of a cumulative dose report for illustration at the output device 190 for visualization to the user. The graphic display 400 can be generally illustrative of the aggregation of the cumulative radiation dose applied to each of the predefined areas of the two-dimensional grid 205 as created relative to the space coordinate system 162 of the predefined space where the image acquisition system 125 and the table 155 and the exposed subject 105 are located.

In particular, the graphic display 400 can include illustrations of a date 404 and duration 406 of multiple runs of angiography imaging procedures 408 that are in the format of interactive graphic icons for selection by the user. With selection of a particular run of the angiography procedure (for example "RUN 4" as shown) the example of the graphic display 400 can further include an a graphic illustration 410 of a three-dimensional model of an orientation of the gantry 145 of the image acquisition system 125, the table 155, and the exposed subject 105 in combination with the calculated intersection 210 of the ionizing radiation beam 120 relative to the calculated orientation of the exposed subject 105 on the table 155. The graphic illustration 410 of the three-dimensional model can show a graphic illustration 412 of the calculated intersection 210 of the ionizing radiation beam 120 relative to the orientation of the exposed subject 105 positioned on the table 155 as well as relative to the orientation (e.g., angular alignment) of the gantry 145 in support of the radiation source 130 and detector 140.

The graphic display 400 can further include a graphic illustration 415 of the mapping of the cumulative dose relative to the two-dimensional grid 205 of predefined areas as calculated by the computer or hardware processor 175 of the system 100 as described above. The illustration of each of the predefined areas 420 that comprise the illustration of the two-dimensional grid dose map 415 can be color-coded or otherwise graphically delineated to show a variation in value of cumulative radiation dose applied as calculated for each intersection 210 of the ionizing radiation beam 120 with the two-dimensional grid 205. The color-coding can be correlated to multiple ranges of value of cumulative radiation dose, or merely to illustrate where the calculated cumulative radiation dose at the respective intersection 210 with the two-dimension grid 205 is at or above a threshold in contrast to below-threshold cumulative radiation dose at other grid areas. For each illustration of the area 420 of the graphic illustration 415 of the two-dimensional grid of cumulative radiation dose applied where a threshold is calculated to be exceeded, the graphic display 400 can show the following: date/time stamp of the procedure 404, a protocol (e.g., coronaries, etc.), type of acquisition mode (e.g., fluoroscopy) (not shown), an auto exposure preference (not shown), frame rate (not shown), image acquisition detail level (not shown), number of runs or scans 408, total duration of each run 406, all in combination with a graphic illustration 424 of the cumulative radiation dose (e.g., ESAK, Gy) and DAP (mGy·cm$^2$) directed to the exposed subject 105. The graphic display 400 can further a graphic illustration (e.g., bar graph) 430 of duration of exposure for the particular run 408 relative to the graphic illustration 432 of the total duration of radiation exposure of the exposed subject 105 to the ionizing radiation beam 120 for the angiographic imaging procedure. This information can be retrieved from the recorded information in the DICOM image file or directly communicated in general real time from the image acquisition system 125, simultaneous for viewing with an illustration 415 of the measure of cumulative radiation dose directed to the exposed subject 105 in correlative time, and provide the user with visual illustration of the point in time of the medical procedure when the graphic illustration 420 shows that the cumulative radiation dose exceeded the threshold.

The embodiment of the cumulative dose two-dimensional map can include an illustration of the measure of cumulative radiation dose (ESAK) directed to the exposed subject during the examination relative to the tracked position or angulation of the radiation source 130 and/or detector 140 of the image acquisition system 125. The tracked position (e.g. angulation) of the radiation source 130 and/or detector 140 can be correlated to the tracked position (e.g., angulation) of the gantry 145 in support of the radiation source 130 or detector 140. The display can illustrate the orientation of the ionizing radiation beam 120 relative to the horizontal axis or vertical axis of the room to represent varied positions of the gantry 145 of the image acquisition system 125 with respect to various orientations of the exposed subject 105 having areas of interest (left/right oblique, cranial/caudal positions, etc.) in the particular imaging procedure, in combination with the time-scale measured cumulative distribution of the radiation dose (e.g., ESAK) to the exposed subject 105. Thereby, the system 100 can illustrate to the user the cumulative dose two-dimensional grid map 415 simultaneously for reference with illustration of the orientation and intersection of the ionizing radiation beam 120 relative to the relative time-scale of the particular imaging procedure on the exposed.

With the user selecting or actuating the graphic icon 408 described above, the system 100 can generate the graphic display 400 with the graphic illustration 410 of the above-described three-dimensional model showing the orientation of the gantry 145 of the image acquisition system 125, the table 155, the exposed subject 105, and the intersection 210 of the ionizing radiation beam 120 as it may vary for each of the received imaging procedure runs or events as recorded in received DICOM image files. According to the example graphic display 400, the user of the system 100 can view the graphic illustration 415 of the cumulative radiation dose map in general simultaneous time scale relation relative to the graphic illustration 424 of the cumulative radiation dose applied to the exposed subject 105 and the graphic illustration 430 of the exposure time relative to the overall exposure time of the angiographic imaging procedure, all in combination with graphic illustration 410 that shows a three-dimensional model of the calculated orientation of the gantry 145 and respective graphic illustration 412 of the intersection 210 of the ionizing radiation beam 120 relative to the orientation of the orientation of the exposed subject 105. Although certain forms of graphic illustrations 424, 430 of the cumulative dose and cumulative exposure time, respectively, are shown, the type of graphic illustrations (e.g., line graph, bar graph, pie chart, etc.) can vary and is not limiting on the subject matter described herein.

The example of the graphic display 400 can further include an illustration (not shown) of the measure of the orientation of the intersection 210 and respective cumulative radiation dose values as mapped on the grid per the distribution of different types of protocols (e.g., imaging of aorta, aorta-arch, coronaries, femoral, other) involving exposure to the ionizing radiation beam 120 per unique identifier of the operator of the image acquisition system 125 and a tracked duration thereof over an extended period of time (e.g., per user input or standard periodic reporting period (e.g., monthly)) and occurrences of threshold exceedance as illustrated on the two-dimensional grid dose map 415. The example graphic display 400 can further include an illustration (not shown) of a frequency of performance (measure of number of occurrences of threshold cumulative radiation dose extended) for different protocols relative to one another and an associated cumulative distribution of cumulative radiation dose to the exposed subject 105.

The system 100 can further be operable to create graphic illustrations (not shown) that visualize the comparison of data from the system 100 relative to data (not shown) of the one or more of the population of ionizing radiation systems associated each of the following: a distribution of a number of events with the image acquisition system 125 where the radiation dose directed to the exposed subject 105 exceeds the threshold radiation dose, a distribution of radiation dose directed to the exposed subject 105 relative to a variance in the source to image distance (SID), a distribution of SID for the image acquisition system 125 relative to a benchmark defined by data acquired from one or more similar types of other imaging systems performing similar protocols or modes of ionizing radiation operation, an auto exposure preference, a frame rate of image acquisition, and a point in time of the examination when the radiation dose exceeded the radiation dose threshold. The system 100 can further create illustrations (not shown) to visualize an individual trend in a history of application of the radiation dose applied to a particular exposed subject 105 or by an individual operator of the image acquisition system 125, and comparing or benchmarking the calculated individual trend relative to a population trend.

The example of the graphic display 400 can further include an illustration (not shown) of measured radiation dose (e.g., cumulative dose, duration of exposure to radiation, DAP (product of dose multiplied by area of radiation beam) directed to the exposed subject 105 and cumulative percentile (%) for comparison relative to type of protocol (aorta, coronaries, imaging of aorta-arch, femoral, foot, lower leg, carotids, etc.), as well as relative to image acquisition mode (e.g., cardiac, fluoroscopy, digital subtraction angiography (DSA), etc.). The example of the graphic display 400 can further include an illustration (not shown) of a distribution of cumulative radiation dose on the two-dimensional grid relative to a benchmark defined by data acquired from one or more similar types of imaging systems, similar protocols of image acquisition, or similar modes of image acquisition or combination thereof.

The system 100 can be further configured to compare one or more types or parameters represented by the acquired data relative to a threshold. For example, the graphic display 400 can show illustrations (not shown) of groupings or categorizations the acquired data or characteristics of the individual image acquisition system 125 for comparison to acquired data from one or more other similar image acquisition systems 125 or similar procedures/tasks/protocol of image acquisition or combination thereof, as well as illustrations (not shown) of a distribution of a number of events (e.g., exams, radiation therapy treatments, etc.) that exceed a certain grouping or threshold range of cumulative radiation dose (e.g., grouped in 1 Gy dose range increments) directed to the exposed subject 105, as well as a measure of number of image acquisitions (e.g., scans, exams) where the measured radiation dose exceeded the cumulative radiation dose threshold.

The example of the graphic display 400 can include a graphic illustration (not shown) of a distribution of cumulative radiation dose directed to the exposed subject 105 relative to variance in the source to image distance (SID) for the image acquisition system 125. This illustration (not shown) can include a benchmark comparison relative to analogous distribution of cumulative radiation dose versus variance in SID for a population of other image acquisition systems 125 of similar type, or employed in similar protocol of mode of image acquisition. The variance in SID (e.g., in centimeters) can be illustrated in groupings along the horizontal axis, and the vertical bar graphic illustration can represent the percentage of total monthly cumulative radiation dose directed (e.g., ESAK, %). From this illustration (not shown), the user of a particular imaging system 125 can better understand from a benchmark perspective a potential reduction in cumulative radiation dose with a change in protocol.

The system 100 can be further configured to identify a proposed response or action (not shown) to reduce the radiation dose to the exposed subject 105, dependent in response to detecting the radiation dose exceeding the threshold according to the status information of the image acquisition system 125 in directing the ionizing radiation beam 120 to the exposed subject 105. The proposed response or action can be generated dependent on acquired data of responses or actions and tracked reduction in cumulative radiation dose to the exposed subject 105 as tracked or measured by one or more other users or other image acquisition systems 125, different from the image acquisition system 125 of interest.

The system 100 can further be operable, in response to calculating a cumulative radiation dose data to exceed a threshold for an angiographic image acquisition event, to trigger automatically communicating the acquired information and the graphic illustration 415 of the two-dimensional grid dose map as well as other contents of the graphic display 400 to the remote office or remote devices 180.

Technical effects of the subject matter described above can include, but is not limited to, providing the system 100 and method to address concerns associated with use of ionizing radiation, and the need for access to data or increased knowledge to manage directing radiation dose to the exposed subject (e.g., patient) 105. This improved access to data can benefit the establishment of standard operating procedures and protocols in the use of ionizing radiation to perform various tasks, as well as benefit the measurement and evaluation of an impact of each procedure's protocol in the likelihood for burn or other late effects associated with exposure to ionizing radiation relative to the characteristics of exposed subjects 105. The system 100 and method of operation described herein can provide This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of mapping a radiation dose applied in an angiography imaging procedure of a patient resting on a table, the method comprising the steps of:

calculating with a computer processor an angulation of a radiation beam applied by an image acquisition system to the patient in the angiography imaging procedure relative to a table in response to a digital signal from the image acquisition system;

calculating with a computer processor an angulation of the table relative to a room coordinate system;

calculating an orientation of the patient resting on the table relative to the room coordinate system;

calculating with a computer processor an intersection of the radiation beam relative to a two-dimensional grid of pre-defined areas at a surface of the table;

calculating with a computer processor the radiation dose applied by the image acquisition system at the intersection of the radiation beam to each of the predefined areas of the two-dimensional grid; and creating a graphic display with a computer processor mapping an aggregation of the radiation dose applied to each of the predefined areas of the two-dimensional grid relative to the patient resting on the table.

2. The method of claim 1, wherein the step of calculating with the computer processor the radiation dose applied by the image acquisition system at the intersection of the radiation beam to each of the predefined areas of the two-dimensional grid is performed not dependent on a pixel data in an image data file associated with the angiography imaging procedure of the patient.

3. The method of claim 1, wherein the step of calculating the radiation dose of the radiation beam applied to each of the predefined areas of the two-dimensional grid is dependent on a plurality of parameters including: a table material, a table material density, a table thickness, a mattress thickness, a mattress material, and a mattress density.

4. The method of claim 1, wherein the step of calculating an intersection of the radiation beam relative to the two dimensional grid of pre-defined areas is dependent on a geometrical relation of a table coordinate system that defines the table with respect to an isocenter of a C-arm of the image acquisition system.

5. The method of claim 1, wherein the step of calculating the orientation of the patient relative to the two-dimensional grid of predefined areas is dependent on an orientation of the patient relative to a table coordinate system and a modifier factor value for an orientation of the patient.

6. The method of claim 1, wherein the step of calculating the intersection of the radiation beam relative to the two dimensional grid of pre-defined areas is dependent on a plurality of parameters including: an acquisition plane of the image acquisition system, a distance of a source of the radiation beam to a detector plan of the image acquisition system, a distance of the source of the radiation beam to an isocenter of a C-arm of the image acquisition system, a collimated field area of a receptor of the image acquisition system, a start angle of orientation of the radiation beam, and an end angle of orientation of the radiation beam.

7. The method of claim 1, wherein the step of calculating the intersection of the radiation beam relative to the two-dimensional grid of predefined areas is dependent on a plurality of parameters including: a longitudinal position of the table relative to the image acquisition system coordinate position, a lateral position of the table relative to the image acquisition system coordinate position, a table height position relative to the image acquisition system coordinate position, an angle of a longitudinal axis of the table coordinate system relative to a horizontal plane, an angle of the vertical axis of the table coordinate system relative to the horizontal plane, and a lateral axis of the table of the table coordinate system relative to the horizontal plane.

8. The method of claim 1, wherein the step of calculating the radiation dose applied by the image acquisition system at the intersection of the radiation beam to each of the predefined areas of the two-dimensional grid is dependent on a type of imaging event with the image acquisition system, wherein the type of imaging event is one of a fluoroscopic image acquisition, a stationary image acquisition, a stepping image acquisition, and a rotational image acquisition.

9. The method of claim 8, wherein the step of calculating the radiation dose applied by the image acquisition system at the intersection of the radiation beam to each of the predefined areas of the two-dimensional grid is further dependent on a time of duration of the type of imaging event as defined in the image file of the patient.

10. The method of claim 1, wherein the step of creating the graphic display with the computer processor illustrative of the aggregation of the radiation dose applied to each of the predefined areas of the two-dimensional grid is created relative to the room coordinate system of a predefined space where the image acquisition system and the table and the patient are located.

11. A system for use in mapping a radiation dose applied in an angiography imaging procedure of a patient, comprising:
    an image acquisition system, comprising a C-arm, that generates a radiation beam in a diagnostic image acquisition of the patient, the image acquisition system defined by an image acquisition system coordinate system;
    a table having a surface in support of the patient during the angiography imaging procedure with the image acquisition system, the table defined by a table coordinate system having a predefined orientation to a room coordinate system;
    a computer processor, comprising a memory, in communication to execute a plurality of programming instructions stored in a memory, the plurality of programming instructions to instruct the computer processor to perform the steps of:
        calculating an angulation of the radiation beam applied by the image acquisition system to the patient in the angiography imaging procedure relative to the table;
        calculating an angulation of the table relative to the room coordinate system;
        calculating an intersection of the radiation beam relative to a two-dimensional grid of pre-defined areas at the surface of the table;
        calculating the radiation dose applied by the image acquisition system at the intersection of the radiation beam to each of the predefined areas of the two-dimensional grid;
        calculating an orientation of the patient relative to the two-dimensional grid of predefined areas; and
        creating a graphic display illustrative of an aggregation of the radiation dose applied to each of the predefined areas of the two-dimensional grid and the orientation of the patient for viewing by a user.

12. The system of claim 11, wherein the step of calculating the radiation dose of the radiation beam applied to each of the predefined areas of the two-dimensional grid dependent on a plurality of parameters including: a table material, a table material density, a table thickness, a mattress thickness, a mattress material, and a mattress density.

13. The system of claim 11, wherein the step of calculating an intersection of the radiation beam relative to the two dimensional grid of pre-defined areas is dependent on a geometrical relation of the table coordinate system with respect to an isocenter of a C-arm of the image acquisition system.

14. The system of claim 11, wherein the step of calculating the orientation of the patient relative to the two-dimensional grid of predefined areas is dependent on an orientation of the patient relative to the table coordinate system and a modifier for an orientation of the patient based contained in an acquired image file of the patient generated by the image acquisition system.

15. The system of claim 11, wherein the step of calculating the intersection of the radiation beam relative to the two dimensional grid of pre-defined areas is dependent on a plurality of parameters acquired in an acquired image file of the patient, the parameters including: an acquisition plane of the image acquisition system, a distance of a source of the radiation beam to a detector plan of the image acquisition system, a distance of the source of the radiation beam to an isocenter of a C-arm of the image acquisition system, a collimated field area of a receptor of the image acquisition system, a start angle of orientation of the radiation beam, and an end angle of orientation of the radiation beam.

16. The system of claim 11, wherein the step of calculating the intersection of the radiation beam relative to the two-dimensional grid of predefined areas is dependent on a plurality of parameters including: a longitudinal position of the table relative to the image acquisition system coordinate position, a lateral position of the table relative to the image acquisition system coordinate position, a table height position relative to the image acquisition system coordinate position, an angle of a longitudinal axis of the table relative to a horizontal plane, and a lateral axis of the table relative to the horizontal plane.

17. The system of claim 11, wherein the step of calculating the radiation dose applied by the image acquisition system at the intersection of the radiation beam to each of the predefined areas of the two-dimensional grid is dependent on a type of imaging event with the image acquisition system as defined in an image file of the patient, wherein the type of imaging event is one of a fluoroscopic image acquisition, a stationary image acquisition, a stepping image acquisition, and a rotational image acquisition.

18. The system of claim 11, wherein the step of calculating the radiation dose applied by the image acquisition system at the intersection of the radiation beam to each of the predefined areas of the two-dimensional grid is further dependent on a time of duration of the type of imaging event as defined in the image file of the patient.

19. The system of claim 11, wherein the step of creating the graphic display illustrative of the aggregation of the radiation dose applied to each of the predefined areas of the two-dimensional grid is created relative to a coordinate system of a predefined space where image acquisition system and the table and the patient are located.

* * * * *